(12) United States Patent
Sullivan

(10) Patent No.: US 9,867,607 B2
(45) Date of Patent: Jan. 16, 2018

(54) TENSIONABLE KNOTLESS LABRAL ANCHOR AND METHODS OF TISSUE REPAIR

(71) Applicant: Arthrex, Inc., Naples, FL (US)

(72) Inventor: Derek C. Sullivan, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 93 days.

(21) Appl. No.: 15/135,459

(22) Filed: Apr. 21, 2016

(65) Prior Publication Data

US 2016/0235396 A1 Aug. 18, 2016

Related U.S. Application Data

(62) Division of application No. 13/920,603, filed on Jun. 18, 2013, now Pat. No. 9,345,471.

(60) Provisional application No. 61/663,024, filed on Jun. 22, 2012.

(51) Int. Cl.
  *A61B 17/04* (2006.01)
  *A61F 2/08* (2006.01)
  *A61B 17/06* (2006.01)

(52) U.S. Cl.
  CPC ...... *A61B 17/0401* (2013.01); *A61B 17/0483* (2013.01); *A61B 17/0485* (2013.01); *A61B 17/0487* (2013.01); *A61B 17/06166* (2013.01); *A61F 2/0811* (2013.01); *A61B 2017/0412* (2013.01); *A61B 2017/0414* (2013.01); *A61B 2017/0445* (2013.01); *A61B 2017/0446* (2013.01); *A61B 2017/0458* (2013.01); *A61B 2017/0464* (2013.01); *A61B 2017/0475* (2013.01); *A61B 2017/0496* (2013.01); *A61B 2017/06185* (2013.01); *A61F 2002/0829* (2013.01); *A61F 2002/0852* (2013.01); *A61F 2002/0888* (2013.01)

(58) Field of Classification Search
  CPC . A61B 17/04; A61B 17/0401; A61B 17/0485; A61B 17/0487; A61B 17/06166; A61F 2002/0829; A61F 2002/0852; A61F 2002/0888; A61F 2/08; A61F 2/0811; A61F 2017/0414; A61F 2017/0445; A61F 2017/0446
  See application file for complete search history.

(56) References Cited

U.S. PATENT DOCUMENTS

| 5,534,011 A | 7/1996 | Greene, Jr. et al. |
| 5,549,613 A * | 8/1996 | Goble ............... A61B 17/1617 408/231 |
| 2007/0135843 A1 | 6/2007 | Burkhart |

(Continued)

FOREIGN PATENT DOCUMENTS

| EP | 0916312 A1 | 5/1999 |
| EP | 2455003 A2 | 5/2012 |
| WO | WO-03022161 A1 | 3/2003 |

*Primary Examiner* — Victor Nguyen
(74) *Attorney, Agent, or Firm* — Blank Rome LLP

(57) ABSTRACT

Methods and constructs for soft tissue to bone repairs employing tensionable knotless anchors, without knot tying. The tensionable knotless anchors may be used by themselves or in combination with additional constructs (which may have a similar or different configuration, i.e., modified according to the specific repair) and with the flexible strands provided through tissue, around tissue, or through and around tissue to be repaired or fixated.

13 Claims, 7 Drawing Sheets

(56) References Cited

U.S. PATENT DOCUMENTS

| | | |
|---|---|---|
| 2008/0167660 A1 | 7/2008 | Moreau et al. |
| 2008/0255613 A1 | 10/2008 | Kaiser et al. |
| 2008/0312689 A1* | 12/2008 | Denham ............ A61B 17/0401 606/232 |
| 2009/0082805 A1 | 3/2009 | Kaiser et al. |
| 2009/0312776 A1 | 12/2009 | Kaiser et al. |

* cited by examiner

TENSIONABLE KNOTLESS LABRAL ANCHOR AND METHODS OF TISSUE REPAIR

CROSS-REFERENCE TO RELATED APPLICATIONS

This is a divisional of U.S. application Ser. No. 13/920,603, filed Jun. 18, 2013, which claims the benefit of U.S. Provisional Application No. 61/663,024 filed Jun. 22, 2012, the disclosures of which are incorporated by reference in their entireties herein.

FIELD OF THE INVENTION

The present invention relates to surgical devices and, in particular, to knotless suture constructs and associated methods of tissue repairs.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

There is a need for knotless suture anchor constructs with improved design that allows tensioning of the tissue after implantation of the suture anchors. Also needed are improved technologies for knotless fixation of soft tissue with easier suture management and increased tensioning of the tissue.

SUMMARY OF THE INVENTION

The present invention provides knotless suture constructs with various designs and methods of fixation of soft tissue to bone with the ability to tension/retension the suture constructs after their implantation. The knotless suture constructs have applicability to soft tissue repairs including labral, rotator cuff, Achilles tendon and biceps, among others.

These and other features and advantages of the invention will be more apparent from the following detailed description that is provided in connection with the accompanying drawings and illustrated exemplary embodiments of the invention.

DETAILED DESCRIPTION OF THE EMBODIMENTS

Figure 1:
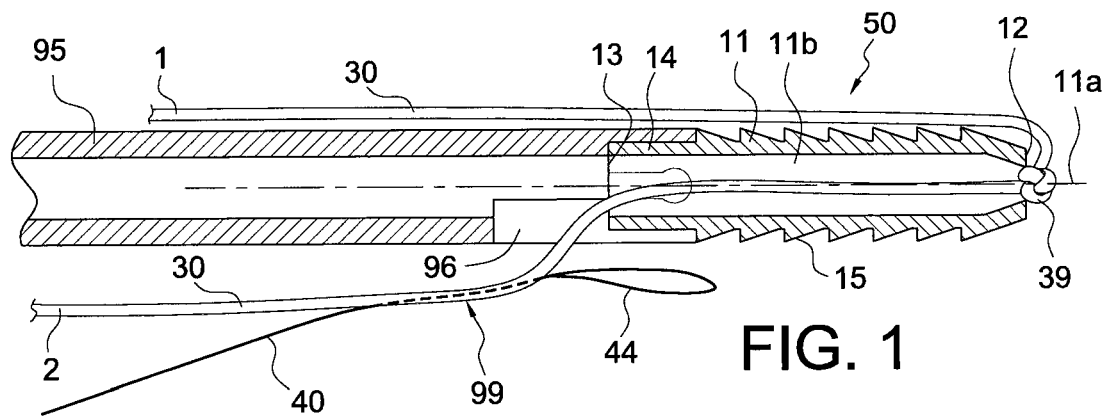
FIGS. 1-4 illustrate a knotless labral suture anchor according to an exemplary embodiment of the present invention (and subsequent steps of tissue repair with such anchor).

The present invention provides knotless suture constructs with various designs and methods of fixation of soft tissue to bone with the ability to tension/retension the suture constructs after their implantation.

In an exemplary embodiment, the knotless suture construct is a tensionable knotless labral anchor that allows for knotless labral repair as well as tensioning after anchor implantation. The labrum can also be attached to the anchor site instead of alongside it. The knotless anchor is a self-cinching construct.

In yet another embodiment, the self-cinching knotless construct has an improved design in that it allows for a significantly smaller diameter anchor to be used, with the splice mechanism being located outside the anchor but within the drill hole, so that the final splice construct will be contained within the bone but not within the anchor body.

In yet an additional embodiment, a tensionable, knotless anchor for rotator cuff repairs is provided which has a design similar to that of the SutureTak® knotless anchor except that the anchor is provided with the splice preloaded (i.e., no suture shuttle instrument is necessary). In this embodiment, the splice is located within the anchor and the suture loop can be made independently from the rest of the construct.

The knotless suture constructs use a mechanism similar to that of knotless anchors detailed and described in U.S. Patent Application Publication No. 2013/0096611 and U.S. application Ser. No. 13/709,138, filed Dec. 10, 2012, the disclosures of both of which are incorporated by reference in their entirety herein, but provide improvements in the design of the anchor constructs (for example, a much smaller diameter anchor) as well as in the suture management and tensioning.

The present invention also provides methods of soft tissue repair which do not require tying of knots and allow adjustment of both the tension of the suture and the location of the tissue with respect to the bone. In the exemplary methods detailed below with reference to FIGS. 1-20, the tensionable knotless anchors are used for labral knotless repairs which allow the labrum to attach to the anchor site and also for tensioning after the anchor implantation. The tensionable knotless anchors detailed below also have an improved design (with a significantly shorter diameter and length) which allows the final splice to be contained outside the anchor body but within the drilled bone hole. The tensionable knotless anchors detailed below may also be provided pre-loaded with the splice, i.e., with no shuttle/pull device attached to the suture (no shuttle/pull device necessary) and with an optional fixed closed loop attached to the spliced suture. The tensionable knotless anchors may be used to achieve simple stitch repairs, mattress stitch repairs or any other suturing repairs such as interlocked looped mattress repairs, among others.

Reference is now made to FIGS. 1-11, which illustrate an exemplary embodiment of a tensionable knotless labral anchor 50 of the present invention that allows for knotless labral repairs as well as tensioning after anchor implantation. Labrum can also be attached to anchor site instead of alongside it.

Tensionable knotless anchor 50 detailed below is provided with an anchor body 11 having a longitudinal axis 11a, a proximal end 13 and a distal end 12, and a plurality of ribs 15 extending circumferentially around it. Cannulation 11b extends along the body 11 to allow passage of flexible strands and of suture passing devices, as detailed below. Cylindrical portion 14 is provided at the proximal end 13 of the anchor 50 and contains a socket 19 configured to securely engage a tip of a driver having a slotted configuration. A flexible strand 30 (suture 30) is provided to pass and slide through the cannulation of the body 11. A shuttle/pull device 40 (suture passing instrument 40 or shuttle 40) provided with eyelet or loop 44 is pre-attached to the flexible strand and provided outside the body 11 of anchor 50.

Tensionable knotless anchor 50 is loaded with tensionable construct 99 (FIG. 1) formed of suture 30 attached to the shuttle/pull device 40. To assemble anchor 50, suture 30, which is typically braided or multi-filament, is preloaded onto the anchor by tying static knot 39, allowing the two free ends (end 1 and end 2) to abut cannulation 11b. Tensionable knotless anchor 50 is loaded onto a driver 95 provided with a slot 96 at its most proximal end, and suture 30 is tied to the driver (for example, wrapped around a cleft of the driver) to fasten tensionable knotless anchor 50 securely to the driver.

Prior to the fastening of the anchor 50 to the driver, suture passing device 40 (for example, a FiberLink™ or a nitinol loop) is threaded through suture 30 (i.e., attached to the suture 30 through splice region 39 located outside body 11). Suture passing device 40 includes an eyelet/loop 44 for passing suture and, optionally, a pull-ring (not shown). Tensionable knotless anchor 50 is loaded with tensionable construct 99 (formed of suture 30 attached to the suture passing device 40). Suture 30 is then passed through or around the tissue 80 which is to be reattached to bone (labrum 80). Suture 30 is subsequently passed through eyelet/loop 44 of the suture passing device 40. Suture passing device 40 is then pulled, thereby pulling suture 30 towards tensionable knotless anchor 50 so that it doubles on itself outside the body of the tensionable knotless anchor. By pulling on one end of the suture 30, the knot 39 is also pulled at the opposite end of the anchor 50 and the splice within the strand 30 (which was formed outside the body of the anchor 50) is now pulled within the body of the anchor 50 (i.e., within the inner diameter of the anchor). Anchor 50 is then secured into bone (for example, into a hole/socket/tunnel formed in the bone) by using the driver.

FIGS. 1-4

FIG. 1: Anchor 50 is loaded onto a slotted driver 95 with suture 30 and suture passer 40 (shuttle/pull device 40). Knot 39 keeps suture 30 from pulling through anchor 50.

Figure 2:
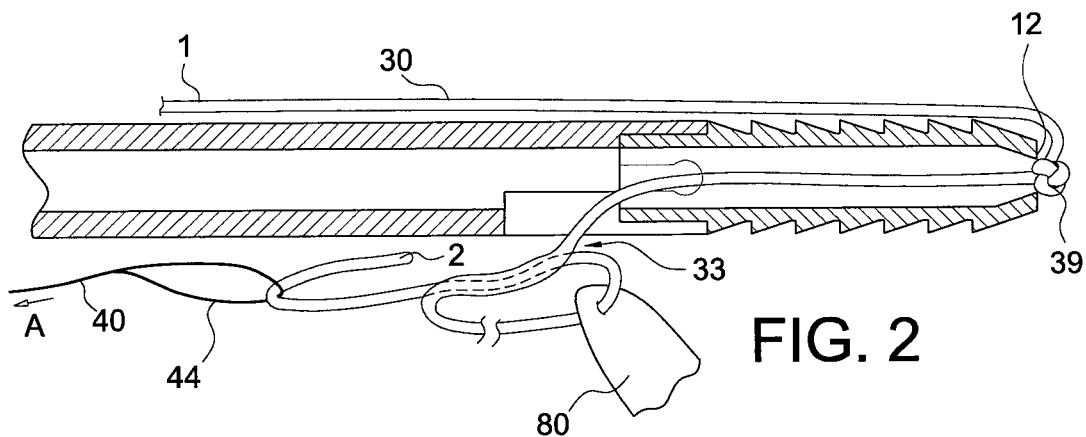

FIG. 2: Suture 30 is passed through tissue 80 and then through eyelet 44 of suture passer 40. The suture passer 40 is pulled in the direction of arrow A and pulls suture free end 2 through itself, creating a suture splice 33 similar to the splice in ACL TR (TightRope®).

Figure 3:
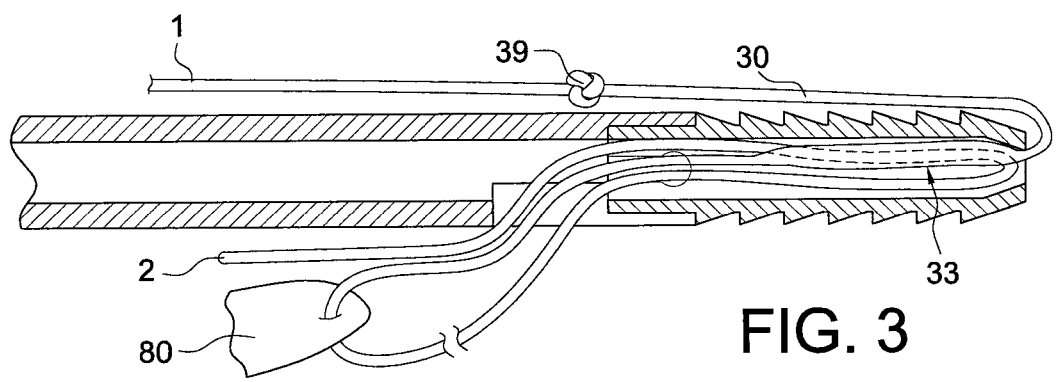

FIG. 3: Free end 1 is pulled, pulling knot 39 to the opposite end of anchor 50 and pulling splice 33 within the inner diameter (ID) of the anchor 50. Anchor 50 with splice 33 positioned within the interior of the anchor body is ready for insertion within bone 90.

Figure 4:
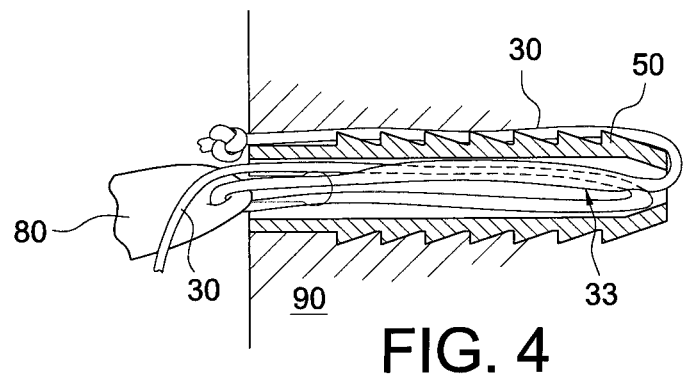

FIG. 4: Free end 1, knot 39 and suture 30 caught between barbs/ribs 15 and bone 90 create an interference that makes that portion stationary against bone 90. Free end 2 can be pulled to remove slack and pull tissue 80 towards anchor 50. Splice 33 will lock in place when tension applied.

FIGS. 5-11

Figure 5:
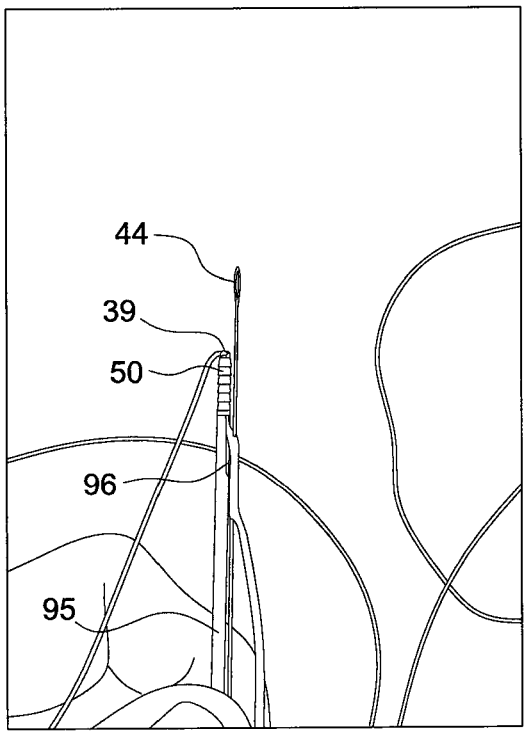
FIGS. 5-11 illustrate steps of assembling the knotless labral suture anchor of FIG. 1 and exemplary steps of a method of tissue repair with such anchor.
Figure 6:
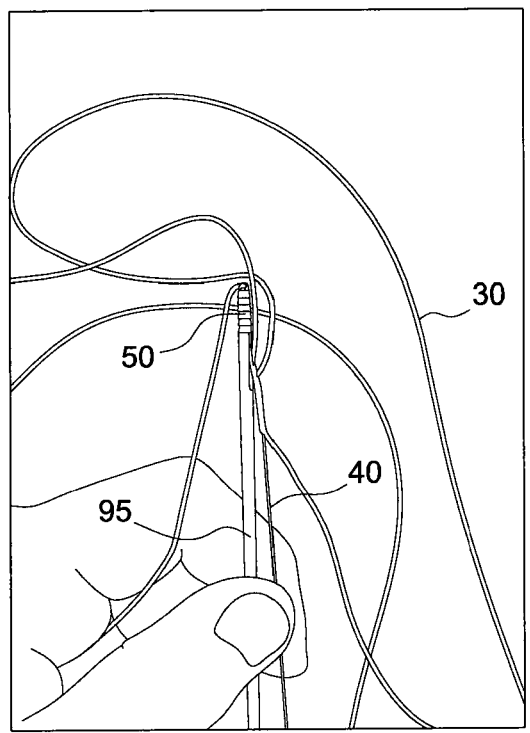
Figure 7:
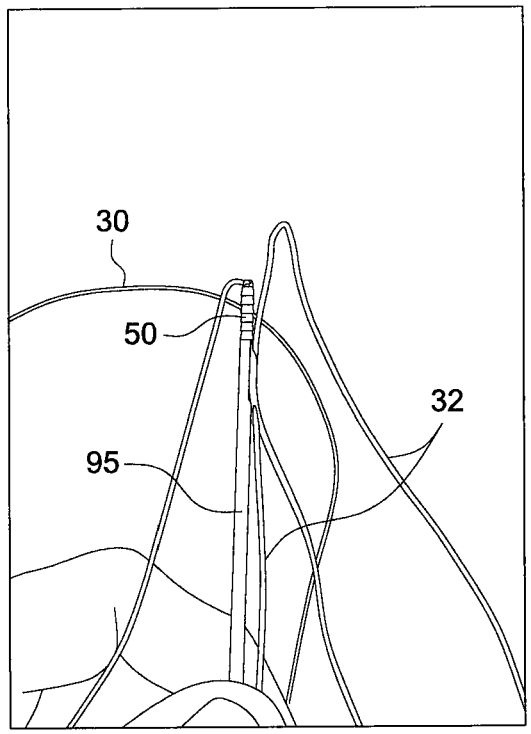

Initial state is a cannulated 3 mm anchor 50 that is set at the tip of a driver 95 (FIG. 5). A slot 96 is cut out at a portion of the tip of the driver 95. Suture 30 is preloaded through the anchor 50 and a knot 39 (likely a FIG. 8 knot 39) is tied at the tip of the anchor 50 (FIGS. 5-7). The portion of suture 30 on the side of the anchor 50 connected to the driver 95 is spliced with a suture passing device 40 (needle, nitinol loop, suture, etc) with eyelet or loop 44 to form splice 33. The remaining suture 30 past the splice 33 is used to pass through tissue 80. Once the free end of suture 30 is passed through tissue 80, the end is passed through the loop/eyelet 44 of the suture passing device 40. The suture passing device 40 is then pulled through the splice, creating a suture only splice that will tighten when created loop 32 is pulled. The knotted end of the suture will prevent the slack from being pulled through the anchor during suture splicing. In a final construct, the suture on the opposite end of the knot 39 will likely be attached to the driver 95 with a mechanism that will pull the suture as described in the next step.

Figure 8:
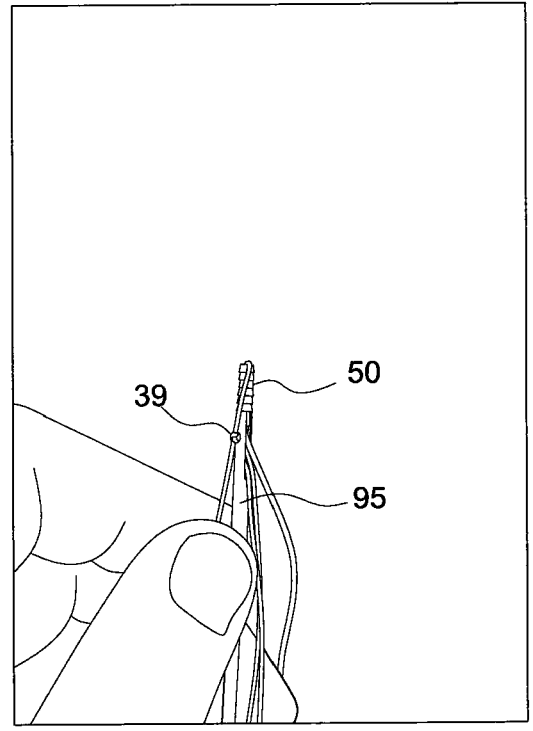

The suture on the knotted side of the anchor is then pulled until it reaches the laser line on the driver. This indicates where the back end of the anchor is. Pulling this knot 39 serves two purposes: (1) it pulls the splice 33 up inside the anchor 50; and (2) it also locates the knot 39 to a point where it will rest outside the anchor 50 and prevent slippage (FIG. 8). The anchor 50 can now be implanted into bone, with the knot 39 resting on the outside of the anchor 50 and the splice 33 residing on the inside (FIG. 8).

Figure 9:
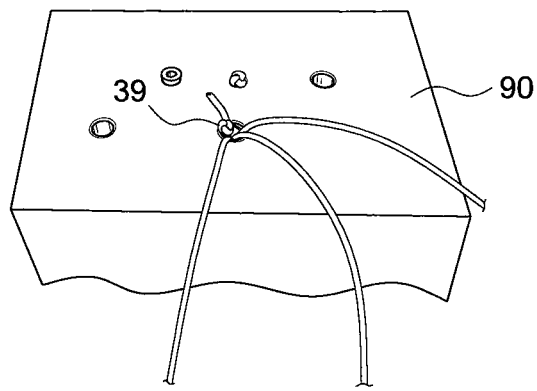
Figure 10:
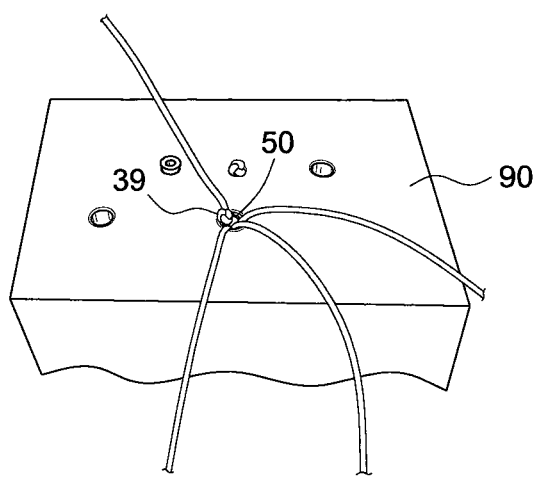
Figure 11:
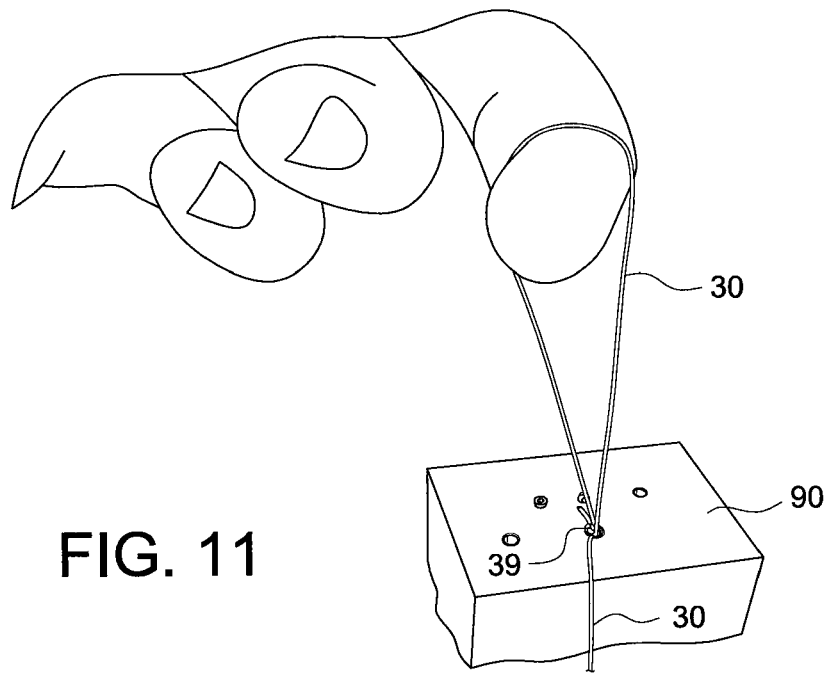

FIGS. 9-11 show exemplary steps of a method of inserting anchor 50 (with knot 39 resting outside the anchor body and splice 33 positioned within the anchor body) within bone 90. The suture 30 can be cut up to the knot 39 and the remaining suture 30 can be pulled until all the slack is taken away from the tissue and the implant (FIG. 11). The forces generated by the tissue tension should lock down movement by tightening the splice 33 within the anchor body.

Reference is now made to FIGS. 12-16 which illustrate another exemplary embodiment of a self-cinching tensionable knotless anchor 150 of the present invention that allows for knotless soft tissue repairs. As detailed below, this knotless anchor construct is a self-cinching construct that has an improved design in that it allows for a significantly smaller diameter anchor to be used, with the splice mechanism being located outside the anchor but within the drill hole so that the final splice construct will be contained within the bone but not within the anchor body. The outer diameter D of the knotless anchor 150 may be about 3 mm or less than 3 mm.

Figure 12:
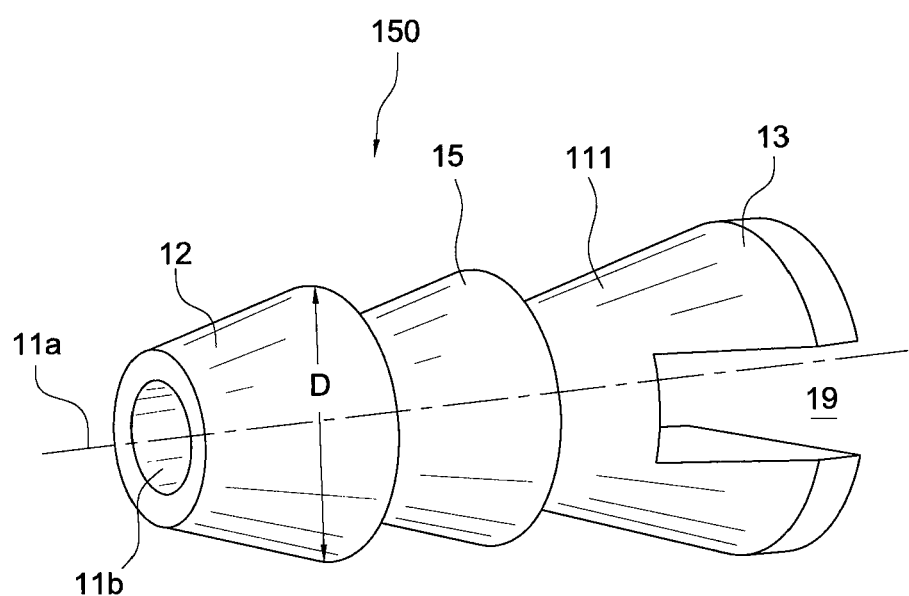
FIG. 12 illustrates a self-cinching tensionable knotless anchor according to another exemplary embodiment of the present invention.

An exemplary perspective view of anchor 150 is shown in FIG. 12. This knotless anchor uses a mechanism similar U.S. Patent Application Publication No. 2013/0096611 and U.S. application Ser. No. 13/709,138, filed Dec. 10, 2012, the disclosures of both of which being incorporated by reference in their entirety herein.

Figure 12A:
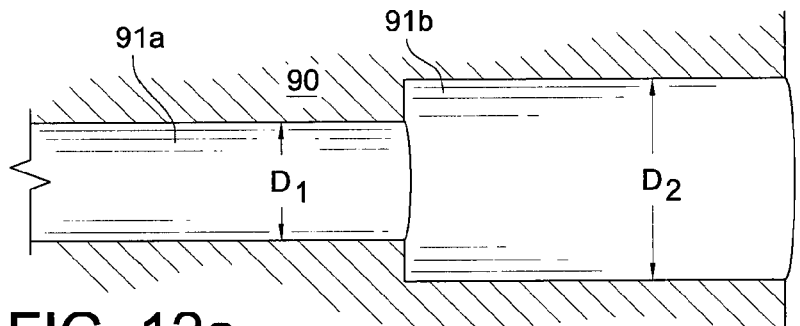
FIG. 12a illustrates a schematic stepped bone tunnel/hole in which the tensionable knotless anchor of FIG. 12 is inserted according to embodiments of the present invention.

The new design of the self-cinching suture knotless construct 150 allows for a significantly smaller diameter anchor to be used, i.e., 3 mm or less. The splice mechanism 33 (FIG. 16) is located outside the anchor 150 but within the drilled bone hole (i.e., within the bone). The suture does not travel around a post or similar structure to lead into the splice. The anchor 150 is significantly shorter in length and diameter. The final splice 33 (FIG. 16) is contained within the bone hole but not within the anchor, allowing for smaller diameter and shorter anchor to be used. An exemplary stepped bone tunnel/hole 91a, 91b formed in bone 90 is illustrated in FIG. 12a. The stepped bone tunnel accommodates anchor 150 pre-loaded with a splice making mechanism, as detailed below.

FIG. 12 illustrates knotless suture anchor 150 of the present invention with exemplary anchor body 111 having a longitudinal axis 11a, a proximal end 13 and a distal end 12, and three exemplary ribs or barbs 15 extending circumferentially around it. Cannulation 11b extends along the body 111 to allow passage of flexible strand(s) and of suture passing device(s), as detailed below. Proximal end 13 of the anchor 150 contains a socket 19 configured to securely engage a tip of a driver 95. A flexible strand 30 (suture 30) is provided to pass and slide through the cannulation of the body 111.

The flexible strand 30 is provided with a pre-loaded splice making mechanism. In an exemplary embodiment, the splice making mechanism is a shuttle/pull device 40 (suture passing instrument 40 or shuttle 40) provided with eyelet or loop 44, pre-attached to the flexible strand and provided outside the body 111 of anchor 150.

Tensionable knotless anchor 150 is pre-loaded with tensionable construct 99 formed of suture 30 attached to the shuttle/pull device 40. To assemble anchor 150, suture 30, which is typically braided or multi-filament, is preloaded onto the anchor by tying static knot 39. Prior to the fastening of the anchor 150 to the driver, suture passing device 40 (for example, a FiberLink™ or a nitinol loop) is threaded through suture 30 (i.e., attached to the suture 30 through splice region 39 located outside body 11). Suture passing device 40 includes an eyelet/loop 44 for passing suture and, optionally, a pull-ring (not shown). Tensionable knotless anchor 150 is loaded with tensionable construct 99 (formed of suture 30 attached to the suture passing device 40).

Once the anchor 150 is implanted into bone, suture 30 is passed through or around the tissue which is to be reattached to bone. Suture 30 is subsequently passed through eyelet/loop 44 of the suture passing device 40. Suture passing device 40 is then pulled, thereby pulling suture 30 towards tensionable knotless anchor 50 so that it doubles on itself outside the body of the tensionable knotless anchor but within the bone hole/socket/tunnel (as detailed below) and forms splice 33.

A method of anchoring the self-cinching suture knotless construct 150 of FIG. 12 into stepped bone tunnel/hole 91a, 91b of FIG. 12a comprises the exemplary steps of:

FIGS. 13-16

Figure 13:
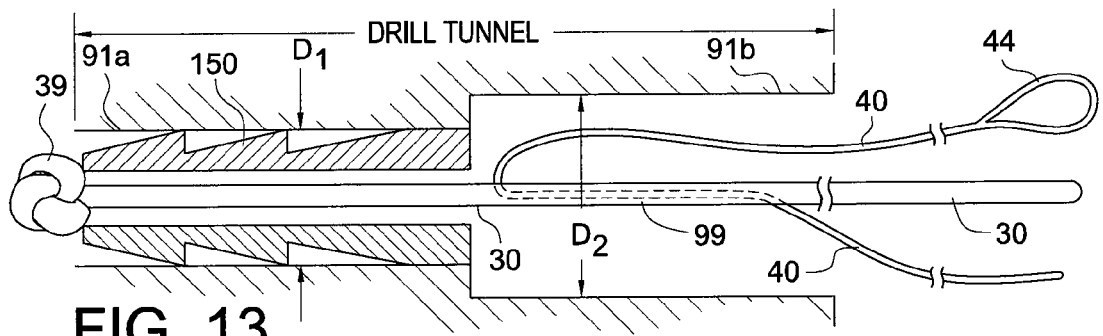
FIGS. 13-16 illustrate subsequent steps of a method of knotless soft tissue repair with the anchor of FIG. 12 inserted into the stepped bone tunnel/hole of FIG. 12a, and according to an exemplary embodiment of the present invention.

FIG. 13: Anchor 150 is implanted in stepped bone tunnel/hole 91a, 91b of bone 90. The bone tunnel/hole 91a, 91b has two diameters, the top portion 91b being larger than the bottom portion 91a where the anchor 150 is implanted, to accommodate the suture splice construct. Diameter D2 of the top portion 91b is greater than diameter D1 of the bottom portion 91a, as shown in FIG. 12a. Preferably, diameter D1 of the bottom portion 91a (bone tunnel 91a) is about equal to outer diameter D (FIG. 12) of anchor 150. The anchor 150 is preloaded with splice making mechanism 40 (shuttle/pull device 40).

Figure 14:
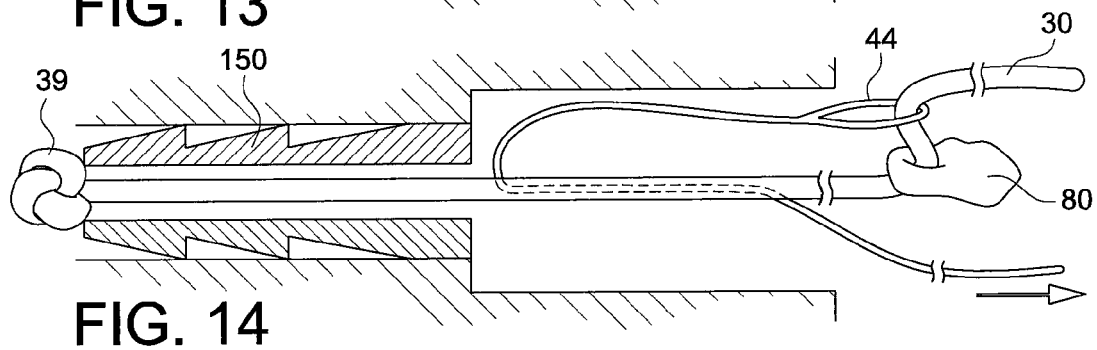

FIG. 14: Similar to previous design, the suture 30 is passed around the tissue 80 and is loaded through the nitinol wire 44 of the suture splicing mechanism 40. Nitinol wire is used to shuttle the suture through itself creating splice 33.

Figure 15:
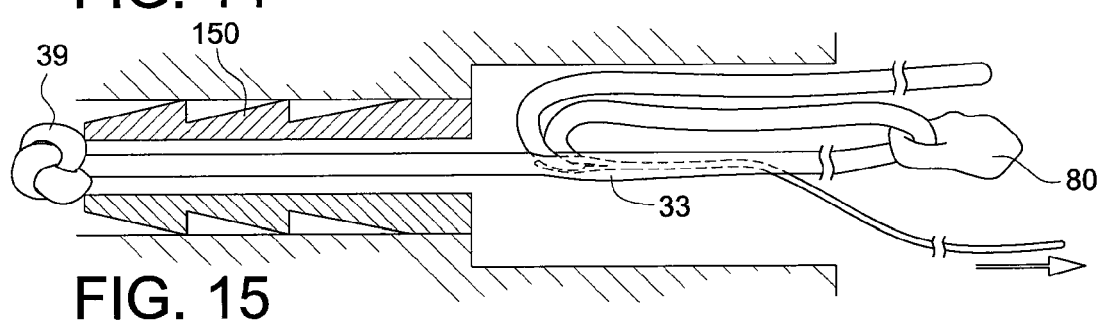
Figure 16:
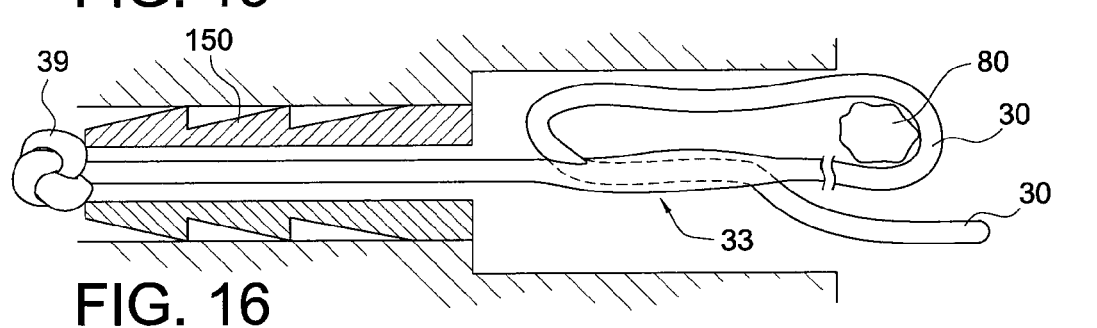

FIG. 15: Similar to previous design, the suture 30 is shuttled through itself creating a splice 33. In this embodiment, there is no "lead-in" from a post. The suture 30 can be tapered to help facilitate pulling it through itself FIG. 16: Same as previous design, tension is pulled until the tissue 80 is positioned in the desired location and under the proper amount of tension as determined by the surgeon. Tensioning the suture 30 makes the locking mechanism within the splice 33 work. The end of the suture 30 is then trimmed.

Reference is now made to FIGS. 17-20 which illustrate subsequent steps of a rotator cuff repair and fixation with another tensionable knotless anchor construct 250 of the present invention which is part of surgical construct 200, similar to U.S. application Ser. No. 13/709,138, filed Dec. 10, 2012, the disclosures of which is incorporated by reference in its entirety herein.

Surgical construct 200 comprises fixation device 250 (suture anchor 250) attached to at least another fixation device 50a (suture anchor 50a). Fixation device 250 is provided with an attached (pre-loaded) tensionable construct formed of flexible strand 30 with a free end 1, a splice 33 (located within the body of the fixation device) with a spliced adjustable loop 32, and a knotted fixed end 39 or insert molded fixed end. An attachment device 35 (in the form of a fixed loop 35 or second loop 35) is attached to the spliced adjustable loop 32 for further attachment to another fixation device 50a (second fixation device 50a).

As in the previously-described embodiments, fixation device 250 is a tensionable knotless anchor having an anchor body 11 provided with a longitudinal axis 11a, a proximal end 13 and a distal end 12, and a plurality of ribs 15 extending circumferentially around it. Cannulation 11b extends along the whole length of body 11 to allow passage of flexible strand 30 and splice 33 and to secure knot 39. Proximal end 13 of the anchor 250 contains a socket 19 (FIG. 20) configured to securely engage a tip of a driver.

Anchor 250 may be a screw-in anchor or a push-in style anchor. Anchor 250 may be formed of metal, biocompatible plastic such as PEEK or a bioabsorbable PLLA material. Socket 19 at the distal end 13 of the anchor 250 is configured to securely engage a tip of a driver, as detailed below. The socket of the anchor 250 may have any shape adapted to receive a driver tip for pushing tap-in or screw-in style anchors. Tensionable knotless anchor 250 may be made of one or more pieces, or may be provided as an integrated device.

Tensionable knotless anchor 250 is preferably provided pre-loaded (pre-assembled) with the tensionable construct. Anchor 250 may be assembled with the tensionable construct by employing a shuttle/pull device 40 (a suture passing instrument such as FiberLink™ or a nitinol loop) attached to the flexible strand 30, as detailed in U.S. Patent Application Publication No. 2013/0096611 and U.S. application Ser. No. 13/709,138, filed Dec. 10, 2012. Static knot 39 (fixed end 39) prevents suture 30 from passing through distal blind hole 12a. The suture may also be preloaded by insert molding or by any other means known in the art.

Tensionable knotless construct also includes a suture loop end 35 which may be in the form of a fixed loop 35 (having a fixed length perimeter) securely attached to the adjustable spliced loop 32 (having an adjustable length perimeter). Second fixation device 50a may be in the form of a fixation device provided with an open eyelet or similar structure, to allow secure engagement of the fixed loop 35. In an exemplary embodiment, the second fixation device is a SwivLock® anchor 50a (as disclosed in U.S. Patent Application Publication No. 2008/0004659, the disclosure of which is incorporated by reference in its entirety herewith) with a distal open eyelet 66a that allows capturing of the fixed loop 35 and further installation into hole 92 in bone 90. The arms 66 of eyelet 66a may be optionally modified to extend away (flare away) relative to a longitudinal axis 61a of body 61 of the second fixation device 50a.

FIGS. 17-20

Figure 17:
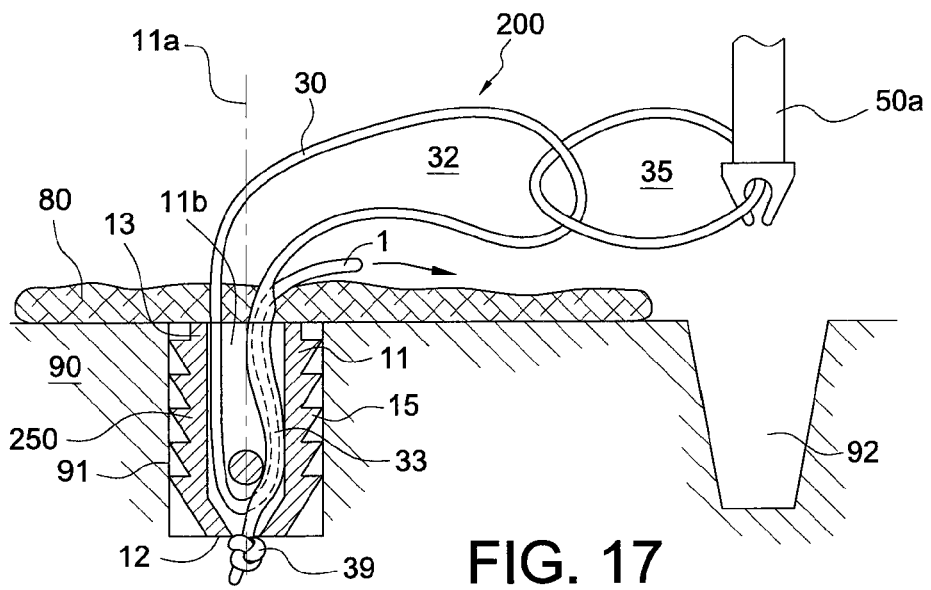
FIGS. 17-20 illustrate subsequent steps of a method of rotator cuff repair with a tensionable knotless anchor according to another exemplary embodiment of the present invention.

FIG. 17: Similar to knotless SutureTak® mechanism, except that the anchor 250 comes with splice 33 preloaded (i.e., no nitinol suture shuttle 40 is necessary). Each anchor can have multiple suture loop constructs loaded on it. Also, connected to the adjustable spliced loop 32, is a fixed closed suture loop 35 which has a fixed length. Anchor 250 is implanted in bone 90 and the suture bundle is passed through the tissue 80. The suture loop 35 (fixed length) is loaded onto eyelet 66a (by passing through the opening formed by arms 66) of Anchor 2 (exemplary SwiveLock® anchor 50a).

Figure 18:
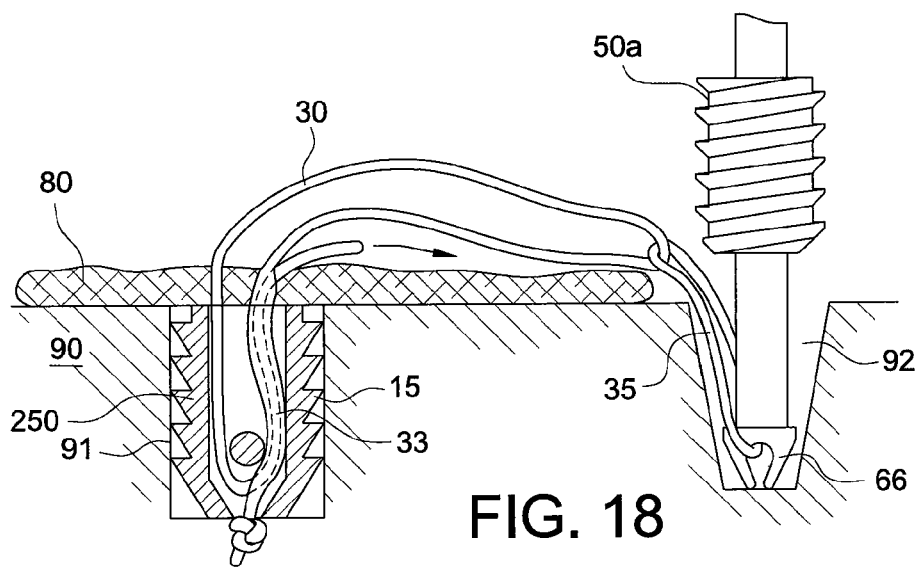

FIG. 18: The suture loops of other anchor(s) can also be loaded onto the eyelet 66a, if desired. Eyelet 66a of Anchor 2 is placed into punched or drilled hole 92 in bone 90. The free end 1 of the suture 30 of the adjustable splice loop 32 (with splice 33) is pulled so that the portion of the fixed loop 35 is exposed outside of the bone hole 92 of Anchor 2.

Figure 19:
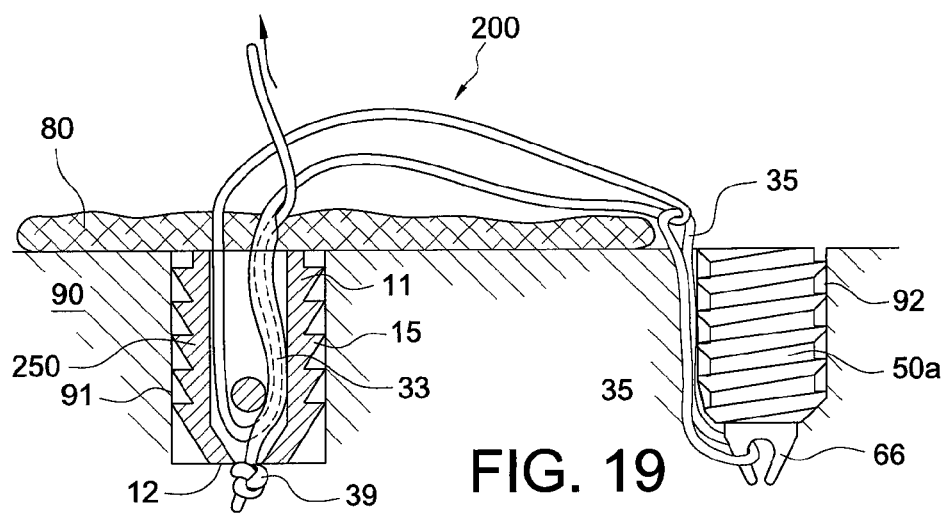

FIG. 19: Anchor 2 is then fully implanted into bone 90 by screwing in or pounding in.

Figure 20:
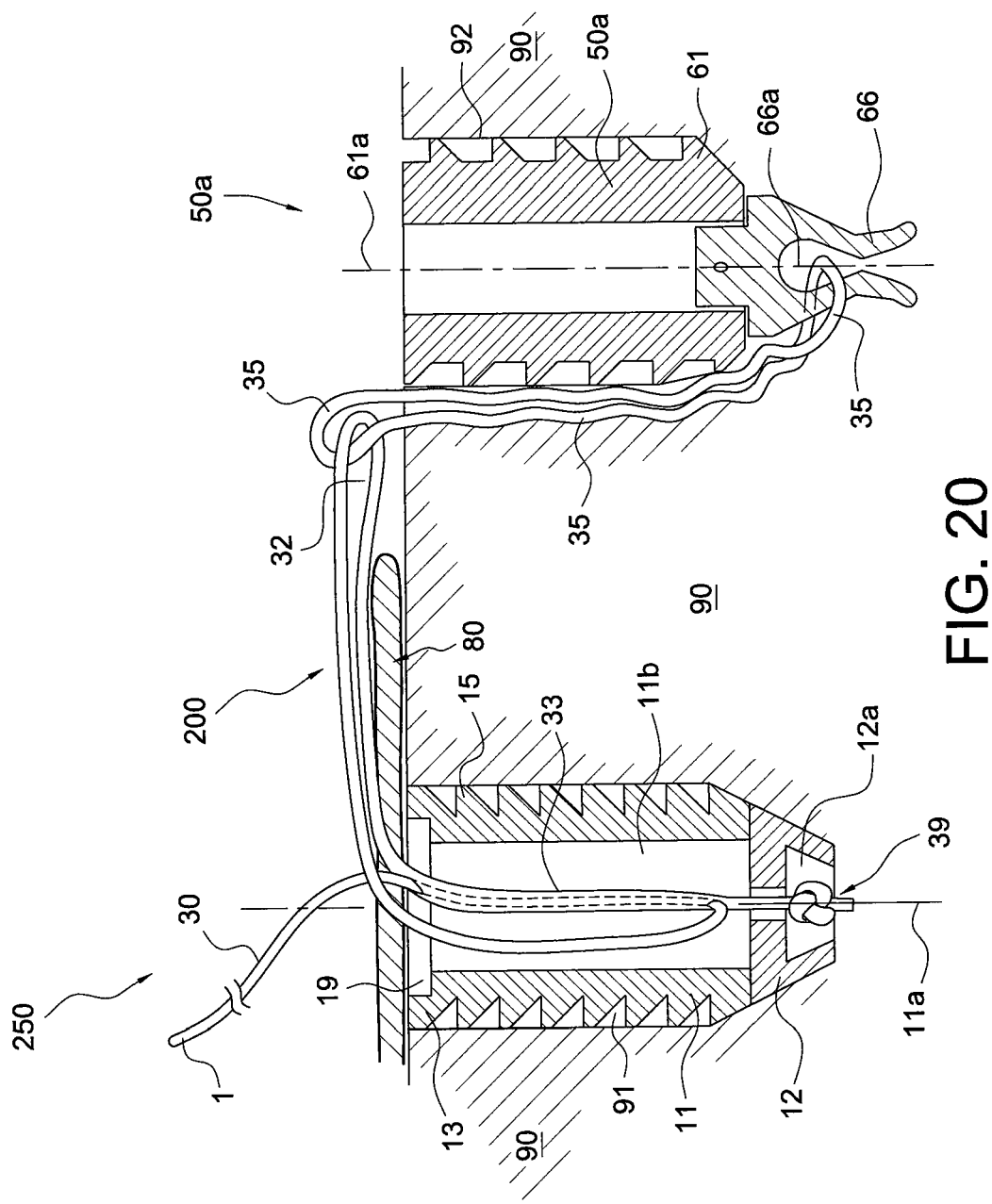

FIG. 20: The tensioning suture is pulled to desired tension and placement of the soft tissue 80. Excess suture 30 is cut.

Improvements of knotless constructs 50, 150, 250 over the previous designs include: no minimum distance between anchors is needed (splice is within anchor); suture loop can be made independently from the construct (easier to manufacture); and suture loop can be FiberWire® (can be different colors to identify double loop splices).

The knotless suture constructs 50, 150, 250 of the present invention may be used in conjunction with knotless anchors, for example, swivel and/or screw-in suture anchors and/or push-in suture anchors (such as an Arthrex SwiveLock® anchor, disclosed in U.S. Patent Application Publication No. 2008/0004659 or a PushLock@ anchor, disclosed in U.S. Pat. No. 7,329,272). The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

The flexible strands may include a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. Typically the suture will be UHWMPE suture without a core to permit ease of splicing. The shuttle/pull device may be a shuttle/pull suture device such as a FiberLink™ or a Nitinol loop.

The strands may also be formed of a stiff material, or combination of stiff and flexible materials, depending on the intended application. The strands may be also formed of suture tape or a combination of suture and tape, depending on the intended application. The strands may be also coated and/or provided in different colors. The knotless anchors of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

Anchor 50, 150, 250 may be a screw-in anchor or a push-in style anchor. Anchor 50, 150, 250 may be formed of metal, biocompatible plastic such as PEEK or a bioabsorbable PLLA material. The socket of the anchor may have any shape adapted to receive a driver tip for tapping or screw-in style anchors. Tensionable knotless anchor 50, 150, 250 may be made of one or more pieces, or may be provided as an integrated device. As detailed above, the tensionable knotless anchor may be modified to carry more than one suture/shuttle construct (i.e., more than a flexible strand 30 and a shuttle/pull device 40), or may be modified to carry only suture.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A method of tissue repair, comprising the steps of:
providing a fixation device comprising a body, a flexible strand extending through the body and a shuttling device attached to the flexible strand, the flexible strand and the attached shuttling device being pre-loaded on the fixation device, the shuttling device being located outside the body of the fixation device;
passing the flexible strand through or around tissue to be fixated and through the shuttling device to form a knotless closed loop having an adjustable perimeter and a splice;
pulling the flexible strand to pull the splice within the body of the fixation device; and
subsequently, installing the fixation device into a socket or hole in bone.

2. The method of claim 1, wherein the step of pulling the flexible strand further comprises providing a knot in the flexible strand at one end of the fixation device, and then moving the knot from the one end of the fixation device to an opposite end of the fixation device.

3. The method of claim 1, wherein the step of pulling the flexible strand further comprises providing tensioning of the tissue relative to the bone.

4. The method of claim 3, wherein the tissue is attached to a site of the bone where the fixation device is installed.

5. The method of claim 4, wherein the tissue is positioned over a most proximal end of the fixation device.

6. The method of claim 1, wherein the tissue is soft tissue.

7. The method of claim 1, wherein the tissue is tendon, labrum, Achilles tendon, rotator cuff, biceps or capsular tissue.

8. The method of claim 1, further comprising the step of adjusting the length of the knotless closed loop to approximate tissue to bone.

9. The method of claim 1, further comprising the steps of:
passing the flexible strand around or through the tissue to be fixated, and then through an eyelet of the shuttling device, wherein one end of the flexible strand is located within the body of the fixation device and the other end is located outside the body of the fixation device;
pulling on the shuttling device to allow the flexible strand to form a splice through itself and outside the body of the fixation device, and provide tensioning of the tissue to be fixated relative to the bone; and
installing the fixation device in bone.

10. The method of claim 9, further comprising the step of securing the flexible strand to the body of the fixation device by providing a knot in the flexible strand, the knot being positioned initially at a distal end of the body of the fixation device.

11. The method of claim 1, wherein the fixation device is an anchor with a cannulation extending in a direction about parallel to the longitudinal axis of the body to allow the flexible strand to be passed through the body of the fixation device.

12. The method of claim 1, wherein the flexible strand is a suture formed of ultrahigh molecular weight polyethylene and wherein the shuttling device is a suture passing instrument.

13. The method of claim 1, wherein the shuttling device is configured to be pulled out of the body of the fixation device to allow the flexible strand to pass through itself and form a splice.

\* \* \* \* \*